United States Patent [19]

Davey et al.

[11] Patent Number: 5,554,517
[45] Date of Patent: Sep. 10, 1996

[54] NUCLEIC ACID AMPLIFICATION PROCESS

[75] Inventors: Cheryl Davey, Toronto; Lawrence T. Malek, Brampton, both of Canada

[73] Assignee: Akzo Nobel N.V., Netherlands

[21] Appl. No.: 386,774

[22] Filed: Feb. 10, 1995

Related U.S. Application Data

[63] Continuation of Ser. No. 211,384, Jun. 24, 1988, Pat. No. 5,409,818.

[30] Foreign Application Priority Data

Feb. 24, 1988 [CA] Canada ..................................... 559709

[51] Int. Cl.$^6$ ............................. C12P 19/34; C12Q 1/68
[52] U.S. Cl. ........................... 435/91.21; 435/6; 435/91.2
[58] Field of Search ............................... 435/91.2, 91.21, 435/6

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 5,409,818 | of/1995 | Davey et al. | 435/91.21 |

FOREIGN PATENT DOCUMENTS

| | | |
|---|---|---|
| 0373960A2 | 6/1990 | European Pat. Off. . |
| 8901050 | 2/1989 | WIPO . |

OTHER PUBLICATIONS

Melton, et al. Nucleic Acids Research 12(8): 7035–7056 (1984).
Lewin "Gene Expression" (1980); Wiley & Sons, New York, NY, pp. 578–582.
Maniatis, et al. "Molecular Cloning" (1982); Cold Spring Harbor Press, Cold Spring Harbor, NY, pp. 128, 214, 215.
Sankor et al. Science 240:331–334 (1989).
Beyer et al. Methods in Enzymology 152:316–325 (1987).

*Primary Examiner*—Stephanie W. Zitomer
*Assistant Examiner*—Ethan Whisenant
*Attorney, Agent, or Firm*—Parkhurst, Wendel & Burr, L.L.P.

[57] ABSTRACT

This invention relates to a process for amplifying a specific nucleic acid sequence. The process involves synthesizing single-stranded RNA, single-stranded DNA and double-stranded DNA. The single-stranded RNA is a first template for a first primer, the single-stranded DNA is a second template for a second primer, and the double stranded DNA is a third template for synthesis of a plurality of copies of the first template. A sequence of the first primer or the second primer is complementary to a sequence of the specific nucleic acid and a sequence of the first primer or the second primer is homologous to a sequence of the specific nucleic acid. The amplification process may be used to increase the quantity of the specific nucleic acid sequence to allow detection, or to increase the purity of the specific nucleic acid sequence as a substitute for conventional cloning methodology.

15 Claims, 6 Drawing Sheets

```
                          T7H1.GAG
AATTCTAATACGACTCACTATAGGGAGACAATAGGCCCTGCATGCACTGGATGTACTCTATCCCAT
----+----:----+----:----+----:----+----:----+----:----+----:----+----
         GATTATGCTGAGTGATATCCCCTCTGTTATCCGGGACGTACGTGACCTACATGAGATAGGGTA
                     T74.PRO

N1.GAG
TCTGCAGCTTCCTCATTGATGGTCTCTTTTAACATTTGCATGGCTGCTTGATGT         124
----+----:----+----:----+----:----+----:----+----:----+
AGACGTCGAAGGAGTAACTACCAGAGAAAATTGTAAACGTACCGACGAACTACAGATC
                              N2.GAG        (H2.GAG)
```

FIG. 2B

```
                     H1.GAG
         GGGAGACAATAGGCCCTGCATGCACTGGATGTACTCTATCCCAT
         ----+----:----+----:----+----:----+----:----
         CCCTCTGTTATCCGGGACGTACGTGACCTACATGAGATAGGGTA

N1.GAG
TCTGCAGCTTCCTCATTGATGGTCTCTTTTAACATTTGCATGGCTGCTTGATGT         124
----+----:----+----:----+----:----+----:----+----:----+
AGACGTCGAAGGAGTAACTACCAGAGAAAATTGTAAACGTACCGACGAACTACAGATC
                              N2.GAG        (H2.GAG)
```

NUCLEIC ACID AMPLIFICATION PROCESS

This is a continuation of application Ser. No. 07/211,384 filed Jun. 24, 1988, now U.S. Pat. No. 5,409,818.

FIELD OF THE INVENTION

This invention relates to a process for amplifying a specific nucleic acid sequence.

BACKGROUND OF THE INVENTION

The detection of a specific nucleic acid sequence present in a sample by probing the sample with a complementary sequence of nucleic acids is a known diagnostic technique. Nucleic acids are highly specific in binding to complementary nucleic acids and are thus useful to determine whether a specific nucleic acid is present in a sample. One must know the sequence of the specific nucleic acid to be detected and then construct a probe having a complementary nucleic acid sequence to the specific nucleic acid sequence.

In this application, the phrase "specific nucleic acid sequence" means a single stranded or double stranded nucleic acid which one wishes to amplify; "sample" means a mixture containing nucleic acids; "sufficiently complementary" means that two nucleic acids, a primer and a template, are capable of specific interaction which allows efficient, primer-dependent and template-directed synthesis of DNA, under given conditions of ionic strength and temperature.

Since nucleic acid probes are highly specific, it is preferable in some situations to probe the nucleic acid sequence itself rather than the protein produced by the nucleic acid sequence. As a particular example, a diagnostic method based solely on protein detection would be unreliable for determining the presence of infectious particles of hepatitis B virus, due to the presence of significant levels of non-infectious antigen particles which lack the DNA genome. In another example, the various subtypes of human papilloma virus found in either pre-cancerous or benign cervical tumors can be distinguished only by the use of nucleic acid probe hybridization. Also, the microbiology of AIDS makes it certain that an assay based on the presence of AIDS specific nucleic acid sequence would be superior as a diagnostic.

The greatest difficulty with applying existing nucleic acid probe technology, and the reason that the utility of the existing probe technology is limited, is the copy number problem. In a virus or cell, for example, there is usually a single copy of a particular gene. This one copy may give rise to many copies of gene product, either RNA or protein. For this reason, diagnostic techniques have often involved probing the protein, since the specific sequence of nucleic acid to be detected may give rise to many thousand copies of protein.

The naturally-occurring high number of ribosomal RNA, up to 100,000 copies per cell, has been used by GenProbe to facilitate diagnosis of certain bacterial pathogens, such as Legionella and Mycoplasma, using nucleic acid probes. However, this strategy cannot be used with non-cellular pathogens, such as viruses. Copy number is a particular problem with the development of a nucleic acid probe method for the detection of AIDS virus, where the integrated provirus may be present in less than one of ten thousand peripheral blood lymphocytes. Thus, if the particular nucleic acid sequence suspected to be present in a sample could be amplified, the copy number problem could be circumvented and probe assays could be more readily used.

In a normal biological sample, containing only a few cells, and consequently only a few copies of a particular gene, it is necessary to utilize an amplification process in order to overcome the copy number problem.

One method to amplify is to 'grow out' the sample, that is, to arrange conditions so that the living biological material present in the sample can replicate itself. Replication increases the quantity of nucleic acid sequences to detectable levels. In the food industry, for example, in order to test processed food for the food-poisoning bacteria Salmonella, food samples must be incubated for a number of days to increase the quantity of nucleic acids. In clinical samples, pathogens must also be allowed to increase their number by growing out over some considerable time.

U.S. Pat. No. 4,683,195 issued on Jul. 28, 1987 to Cetus Corporation and U.S. Pat. No. 4,683,202 issued on Jul. 28, 1987 to Cetus Corporation are each directed to a process for amplifying a target nucleic acid sequence contained in a sample. U.S. Pat. No. 4,683,195 relates to a process in which a sample suspected of containing a target nucleic acid sequence is treated with oligonucleotide primers such that a primer extension product is synthesized which in turn serves as a template, resulting in amplification of the target nucleic acid sequence. The primer extension product is separated from the template in the preferred embodiment using heat denaturation. Similarly, U.S. Pat. No. 4,683,202 relates to a process for amplifying a target nucleic acid sequence having two separate complementary strands. The process includes treating the strands with primers to synthesize extension products, separating the primer extension products from the templates, and in turn using the primer extension products as templates.

Both of the above United States patents require either manual or mechanical participation and multi-step operations by the user in the amplification process. The steps involved in these patents require the user to heat the sample, cool the sample, add appropriate enzymes and then repeat the steps. The temperature changes cause the enzymes to loose their activity. Hence, the user is required to repeatedly supplement the amplification mixture with aliquots of appropriate enzymes during the amplification process.

In addition, in U.S. Pat. Nos. 4,683,195 and 4,683,202 each cycle of the amplification process takes place by the synthesis from a first template, of a second template, the second template in turn is used to synthesize the first template. This procedure is repeated, thus, each cycle of the amplification process is based on the synthesis of one product from one substrate.

Notwithstanding the amplification processes disclosed in the prior art, a need exists for improvements to the amplification process. It would be preferable if the amplification process required less participation and fewer manipulations by the user. Further, it would be advantageous if the amplification took place at a relatively constant ambient temperature so that the activity of the enzymes involved in the process would not be affected. It would be more expedient if a template could be used to generate more than one product from one substrate in each cycle of the amplification process.

SUMMARY OF THE INVENTION

This invention relates to an amplification process which is expedient and requires less participation and fewer manipulations by the user of the process than conventional amplification processes. The amplification takes place at a relatively constant ambient temperature. In addition, each cycle of the process generates a plurality of copies of product from one substrate. The amplification process of this invention may be used to increase the quantity of a specific nucleic acid thus circumventing the copy number problem. Hence, probe assays may be more readily used. The amplification process could also be used to increase the purity of a specific nucleic acid sequence as a substitute for conventional cloning methodology.

According to one aspect of the invention, a process for amplifying a specific nucleic acid sequence is used. The process involves the synthesis of single-stranded RNA, single-stranded DNA, and double stranded DNA. The single stranded RNA is a first template for a first primer. The single stranded DNA is a second template for a second primer. The double stranded DNA is a third template for the synthesis of a plurality of copies of the first template. A sequence of the first or the second primer is sufficiently complementary to a sequence of the specific nucleic acid sequence and a sequence of the first or the second primer is sufficiently homologous to a sequence of the specific nucleic acid sequence. A 3' end of the first primer is oriented towards a 3' end of the second primer on complementary strands.

According to another aspect of the invention, a process for amplifying a specific nucleic acid sequence is used. The process involves:
(a) hybridizing a first primer to a first template. The first primer has a DNA sequence which is sufficiently complementary to a RNA sequence of the first template;
(b) synthesizing a first DNA sequence covalently attached to the first primer and complementary to the RNA sequence of the first template. The first DNA sequence and the first primer comprise a second template;
(c) separating the first template from the second template to allow hybridization of a second primer;
(d) hybridizing the second primer to the second template. The second primer has a DNA sequence which is sufficiently complementary to a DNA sequence of the second template. The second primer also has an antisense sequence of a promoter and an antisense sequence of a transcription initiation site for a RNA polymerase;
(e) synthesizing a second DNA sequence covalently attached to the second primer and complementary to the DNA sequence of the second template and synthesizing a third DNA sequence covalently attached, to the second template and complementary to the DNA sequence of the second primer. The second and third DNA sequences, the second primer and the second template comprise a third template;
(f) synthesizing a plurality of copies of the RNA sequence of the first template from the third template.
A sequence of the first or the second primer is sufficiently complementary to a sequence of the specific nucleic acid sequence and a sequence of the first or the second primer is sufficiently homologous to a sequence of the specific nucleic acid sequence. A 3' end of the first primer is oriented towards a 3' end of the second primer on complementary strands.

In a further alternative of the invention, the second primer of DNA has a sequence at its 3' end which is sufficiently complementary to the DNA sequence of the second template. The second primer has at its 5' end an antisense sequence of a promoter and an antisense sequence of a transcription initiation site for a RNA polymerase.

In a further alternative of the invention, the third DNA sequence covalently attached to the second template is complementary to the DNA sequence at the 5' end of the second primer.

In another alternative of the invention, a process for amplifying a specific nucleic acid sequence is used. The process involves combining a first primer, a second primer, ribonuclease H, a RNA-directed DNA polymerase, a DNA-directed DNA polymerase, a RNA polymerase, ribonucleoside triphosphates and deoxyribonucleoside triphosphates with a sample. The first primer of DNA has a sequence which is sufficiently complementary to a first template of RNA. The second primer of DNA has a sequence which is sufficiently complementary to a second template of DNA, and an antisense sequence of a promoter and an antisense sequence of a transcription initiation site which are recognized as substrate by the RNA polymerase. A sequence of the first primer or the second primer is sufficiently complementary to a sequence of the specific nucleic acid sequence and a sequence of the first primer or the second primer is sufficiently homologous to a sequence of the specific nucleic acid. A 3' end of the first primer is oriented towards a 3' end of the second primer on complementary strands.

In a further alternative of the invention, a process for amplifying a specific nucleic acid sequence is used. The process involves adding a first primer, a second primer, avian myeloblastosis viral polymerase, E. coli ribonuclease H, bacteriophage T7 RNA polymerase, ribonucleoside triphosphates and deoxyribonucleoside triphosphates to a sample. The first primer of DNA has a sequence which is sufficiently complementary to a first template of RNA. The second primer of DNA has a sequence which is sufficiently complementary to a second template of DNA, and an antisense sequence of a promoter and an antisense sequence of a transcription initiation site which are recognized as substrate by T7 RNA polymerase. A sequence of the first primer or the second primer is sufficiently complementary to a sequence of the specific nucleic acid sequence and a sequence of the first primer or the second primer is sufficiently homologous to a sequence of the specific nucleic acid sequence. A 3' end of the first primer is oriented towards a 3' end of the second primer on complementary strands.

BRIEF DESCRIPTION OF THE DRAWINGS

In drawings which illustrate embodiments of the invention,

FIG. 2 shows the synthetic oligonucleotides DNA sequences which are used for testing the amplification process.

DETAILED DESCRIPTION OF THE PREFERRED EMBODIMENTS

Figure 1:
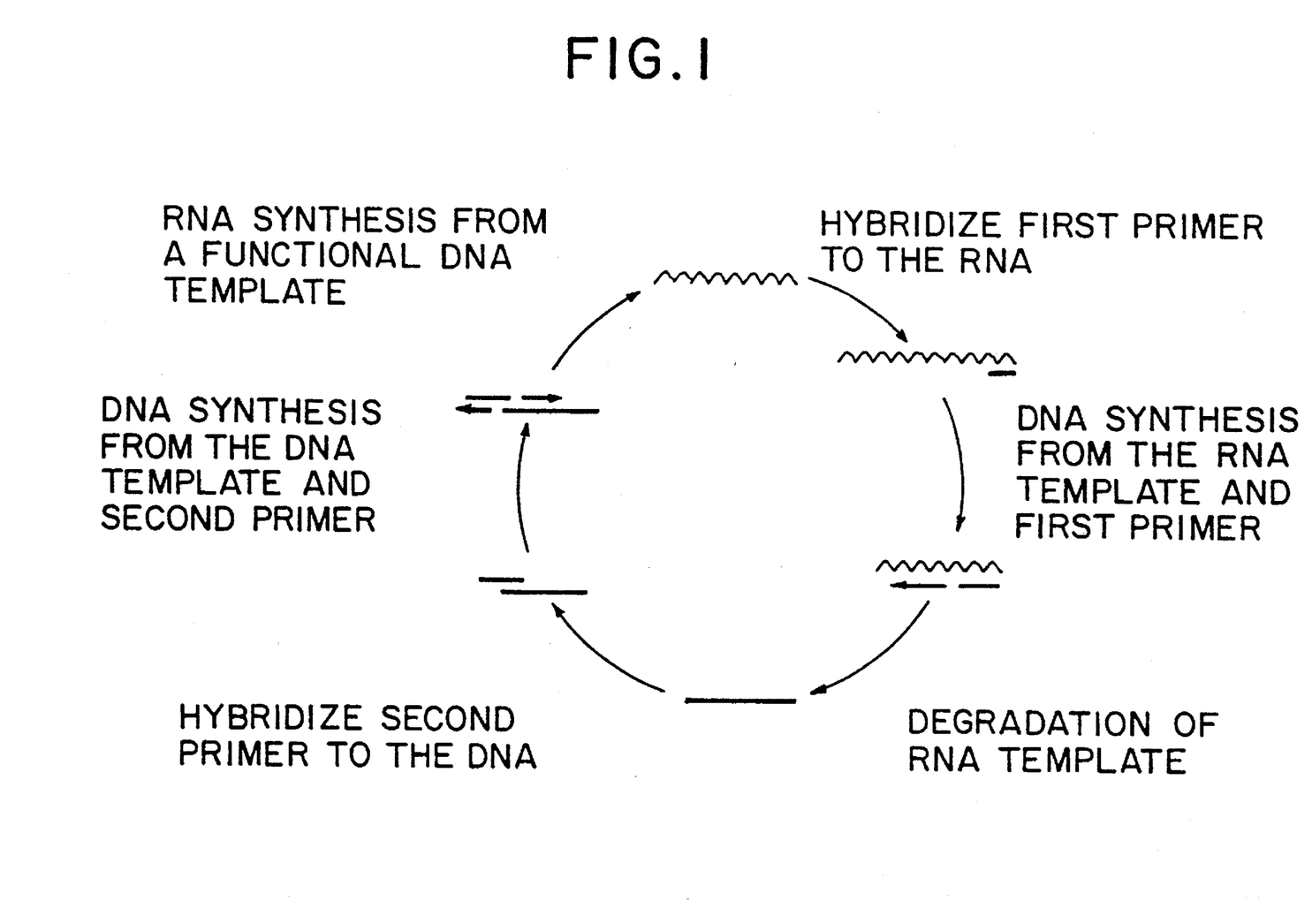
FIG. 1 is a general illustration the nucleic acid amplification process.

This invention relates to a process for amplifying a specific nucleic acid sequence. The amplification involves the alternate synthesis of DNA and RNA and is generally illustrated in FIG. 1. In this process, single-stranded RNA is converted to single-stranded DNA which in turn is converted to a functional template for the synthesis of a plurality of copies of the original single-stranded RNA. A first primer and a second primer are used in the amplification process. A sequence of the first primer or the second primer is sufficiently complementary to a sequence of the specific nucleic acid sequence and a sequence of the first or the second primer is sufficiently homologous to a sequence of the specific nucleic acid sequence. In some instances, both the first primer and second primer are sufficiently complementary and sufficiently homologous to a sequence of the specific nucleic acid sequence, for example, if the specific nucleic acid sequence is double stranded DNA.

The RNA is converted to single-stranded DNA by hybridizing an oligonucleotide primer (the first primer) to the RNA (the first template) and synthesizing a complementary strand of DNA from the first primer, (the first DNA sequence) by using a RNA-directed DNA polymerase. The resulting single-stranded DNA (the second template) is separated from the first template by, for example, hydrolysis of the first template and by using a ribonuclease which is specific for RNA-DNA hybrids (for example, ribonuclease H). The second template is converted to a form which is capable of RNA synthesis by hybridizing a synthetic oligonucleotide (the second primer), which contains at its 3' end a sequence which is sufficiently complementary to the 3' end of the second template and toward its 5' end a sequence containing the antisense strand of a promoter and antisense sequence of a transcription initiation site, and by synthesizing a second DNA sequence covalently attached to the 3' end of the second primer using the second template as a template and synthesizing a third DNA sequence covalently attached to the 3' end of the second template using the second primer as a template, using DNA-directed DNA polymerase. The resulting functional derivative of the second template, which is a third template, is used for the synthesis of a plurality of copies of RNA, the first template, by using a RNA polymerase which is specific for the . promoter and transcription initiation site defined by the second primer. Each newly synthesized first template can be converted to further copies of the second template and the third template by repeating the cycle. In addition, repetition of the cycle does not require participation or manipulation by the user.

The amplification process commences with the addition of a suitable template nucleic acid to the appropriate enzymes, primers, and cofactors under the appropriate reaction conditions. This template nucleic acid is in a form which is capable of homogenous and continuous amplification and can function as an intermediate in the cycle set forth in FIG. 1. The amplification process involves the net consumption of precursors (primers, ribonucleoside triphosphates and deoxyribonucleoside triphosphates) and the net accumulation of products (RNA and DNA). The processes of RNA and DNA synthesis will proceed asynchronously until sufficient levels of nucleic acids have been synthesized to allow detection. The amplification process may be monitored by, for example, the synthesis of a labeled product from a labeled precursor.

It is contemplated that amplification may involve another process either in addition to or in place of the one generally illustrated in FIG. 1. Also possible are certain counterproductive enzymatic reactions which occur at permissibly low rates. Included among the possible non-productive side reactions is the synthesis of RNA and/or DNA in the absence of an added template nucleic acid. Such RNA and/or DNA products can be discriminated from desired products by determining whether a particular sequence which would be found only between the two priming sites of the specific nucleic acid sequence is present.

The first primer is an oligodeoxyribonucleotide which has at its 3' end a sequence which is sufficiently complementary to the 3' end of the first template. The sequence at the 3' end of the first primer has a particular length and base composition to allow specific and efficient synthesis of the first DNA sequence, under the given conditions of ionic strength and temperature. The first primer may be sufficiently complementary to a region internal to the 3' end of the first template in the first cycle. In subsequent cycles, the 5' end of the first primer would be complementary to the 3' end of the first template. It is contemplated that the first primer may be composed partially or completely of nucleotides or nucleotide analogs other than the natural deoxyribonucleotides. The 5' end of the first primer may contain sequences which are not complementary to the first template in the first cycle. The non-complementary sequences may be complementary to a nucleic acid which can be immobilized, or to which can be bound a useful non-nucleic acid component, such as a reporter to facilitate detection. Alternatively, the non-complementary sequences may include an antisense sequence of a promoter and an antisense sequence of a transcription initiation site, which could be used for the synthesis of RNA. This RNA would be complementary to the first template and could be used as an intermediate in another amplification cycle.

The second primer is an oligodeoxyribonucleotide which contains at its 3' end a sequence which is sufficiently complementary to the 3' end of the second template. The second primer has a particular length and base composition to allow specific and efficient synthesis of the second and third DNA sequences, under the given conditions of ionic strength and temperature. In addition, the second primer contains the antisense sequence of a functional promoter and the antisense sequence of a transcription initiation site. This sequence, when used as a template for synthesis of the third DNA sequence, contains sufficient information to allow specific and efficient binding of a RNA polymerase and initiation of transcription at the desired site. The promoter sequence may be derived from the antisense strand of a functional promoter. The transcription initiation site may be derived from the 5' terminal sequence of a natural RNA transcript. In the preferred embodiment, the 5'-terminal sequence of the second primer is AATTCTAATACGACTCACTATAGGGAG. This sequence contains the antisense sequence of the promoter and the antisense sequence of the transcription initiation site for T7 RNA polymerase. Alternatively, the transcription initiation site and promoter for another phage RNA polymerase may be used. In addition, sequences which are unrelated to the promoter function may be included at the 5' end of the second primer or between the transcription initiation site and the sequence at the 3' end which hybridizes to the second template. It is contemplated that the second primer may be composed partially or completely of nucleotides or nucleotide analogs other than natural deoxyribonucleotides.

All of the enzymes used in this invention should meet certain practical specifications. Each enzyme or enzyme preparation should be free of deleterious deoxyribonuclease ("DNase") activities, such as the 5' or 3' exonuclease activities which are often associated with certain DNA polymerases and single-strand or double-strand specific exonuclease or endonucleases. Each enzyme or enzyme preparation should be free of deleterious ribonuclease ("RNase") activities, with the exception of the preferred addition of a ribonuclease activity which is specific for hybrids of RNA and DNA (for example, ribonuclease H). In addition, each enzyme should be reasonably active under the common reaction conditions which are used for the other enzymatic processes, and non-enzymatic processes, such as hybridizing oligonucleotide primers to the RNA or DNA templates.

The DNA-directed RNA polymerase which is used in this invention may be any enzyme capable of binding to a particular DNA sequence called a promoter and specifically initiating in vitro RNA synthesis at a defined initiation site within close proximity to the promoter. The promoter and the initiation site form part of the second primer. In addition the RNA polymerase should be capable of synthesizing several copies of RNA per functional copy of template in a reasonable amount of time. In the preferred embodiment, the bacteriophage T7 RNA polymerase is used. In addition other bacteriophage RNA polymerases, such as phage T3, phage ØII, Salmonella phage sp6, or Pseudomonas phage gh-1 may be used. In another embodiment, other prokaryotic or eukaryotic DNA-directed RNA polymerase may be used. It should be understood that if alternative RNA polymerases are used, then the necessary changes to the promoter and initiation sequences of the second primer should be made according to the template specificity of the particular RNA polymerase.

The RNA-directed DNA polymerase which is used in this invention may be any enzyme capable of synthesizing DNA from an oligodeoxyribonucleotide primer and a RNA template. In addition this enzyme may contain activities for DNA-directed DNA polymerase and RNase H. In the preferred embodiment, the avian myloblastosis viral polymerase ("AMV reverse transcriptase") is used. In addition, the RNA-directed DNA polymerase could be from another retrovirus, such as Moloney murine leukemia virus. Alternatively, other eukaryotic RNA-directed DNA polymerases could be used.

The DNA-directed DNA polymerase which is used in this invention may be any enzyme capable of synthesizing DNA from an oligodeoxyribonucleotide primer and a DNA template. This enzyme should not contain either 5'- or 3'-exonuclease activities, which are associated with many types of DNA polymerase. In the preferred embodiment, the AMV reverse transcriptase is used. However, other DNA-directed DNA polymerases which naturally lack the 5'- or 3'-exonuclease activities could be used. These could include certain eukaryotic DNA polymerases, such as, DNA polymerase α or β those DNA polymerases which could be isolated from a mammalian tissue, such as calf thymus. An otherwise unsuitable DNA polymerase could be made useful by removing the undesirable exonuclease activities either by alteration of the DNA polymerase gene followed by expression of the altered polymerase in a suitable host cell, or by chemical modification of the DNA polymerase protein. Altered versions of DNA polymerase could be made from the Klenow fragment of E. coli DNA polymerase I or the bacteriophage T7 DNA polymerase. It should be understood that such alternative DNA-directed DNA polymerase activities are added to supplement the activity contributed by the RNA-directed DNA polymerase, since in the preferred embodiment, both RNA-directed and DNA-directed DNA polymerase activities are supplied by the same enzyme.

The RNase H which could be used in this invention may be any enzyme capable of hydrolyzing a RNA which is annealed to a complementary DNA. This enzyme should not be capable of hydrolyzing single or double-stranded RNA or any DNA. In the preferred embodiment, the E. coli RNase H is used. In addition, other RNase H enzymes could be used, such as calf thymus RNase H. Since RNase H is an intrinsic activity of AMV reverse transcriptase, the E. coli RNase H will be supplemented in the preferred embodiment by the RNase H of AMV reverse transcriptase. Alternatively, any other enzyme capable of separating the second template from the first template could be used.

The abovementioned enzymes and primers are mixed together in a reaction vessel which contains the necessary buffers and cofactors for both DNA and RNA synthesis. In addition, the ionic conditions and reaction temperature should be compatible with specific hybridization of the primers to the DNA and RNA templates as is known to those skilled in the art. The reaction mixture should be free of such agents which would interfere with the amplification process, specifically substances which could greatly inhibit the activity of the enzymes, interfere with the hybridizing of primers and templates, or degrade non-productively the nucleic acid intermediates and products.

The description of possible detection schemes may be useful to the application of the amplification process. It should be understood that schemes which may be used for detecting the nucleic acids which are synthesized in the amplification process are not limited to those described herein, and it is contemplated that other methods may be used.

In one embodiment, a labeled precursor may be added to the reaction mixture. Amplification is determined by quantitive or qualitative analysis of labeled products, which can be separated from the labeled precursor by using methods known in the art. A labeled precursor may be a ribonucleoside triphosphate for detecting RNA synthesis, or a deoxynucleoside triphosphate or an oligonucleotide primer for detecting DNA synthesis. The type of label may be a radioisotope or a useful chemical group, such as biotin, a chromophore, a fluorophore, or a hapten which could bind to an antibody, or possibly a protein or an enzyme. The labeled products may be separated from the labeled precursors on the basis of solubility, charge, or size. In addition, the labeled DNA or RNA may be hybridized to a nucleic acid which contains a complementary sequence and which can be immobilized.

In another embodiment, the products of the amplification process may be bound to an immobilized support, hybridized to a nucleic acid probe containing a complementary sequence, and separated from the unhybridized nucleic acid probe which remains in solution. The products, DNA or RNA, may be bound directly to a solid support by any stable interaction, such as hydrophobic, electrostatic, or covalent interaction. In addition, the products may contain certain chemical groups, for example, biotin, which may be incorporated into the products during the amplification process to allow binding to an immobilized protein, for example, avidin or streptavidin. In addition, the products may be hybridized to a nucleic acid which contains a complementary sequence and which can be immobilized. The nucleic acid probe would contain a complementary sequence which forms a sufficiently stable interaction with a product of the amplification process to allow binding under the conditions of hybridization and sustained binding under the conditions used for removal of the unhybridized nucleic acid probe. In the preferred embodiment the complementary sequence would be derived from that part of the specific nucleic acid sequence which is between the sequences of the first primer and the second primer. The nucleic acid probe may be a single-stranded DNA or RNA, or a double-stranded DNA or RNA which can be made single-stranded, or an oligonucleotide which can be composed of deoxyribonucleotides and/or ribonucleotides. In addition, the nucleic acid probe may contain a chemical group which could covalently bind to a product DNA or RNA under the appropriate conditions. The nucleic acid probe may be labeled with a radioisotope or a useful chemical group, such as biotin, a chromophore, a fluorophore, or a hapten which could bind to an antibody. In addition, the nucleic acid probe could be conjugated to a protein or enzyme, for example, a phosphatase or a peroxidase. In addition, the nucleic acid probe may contain sequences which would allow in vitro replication of the probe.

It is contemplated that the products of the amplification process may be analyzed by methods which are typically used for nucleic acids that have been enriched by molecular cloning techniques. In one alternative, the synthesis of a specific DNA sequence may be detected by digestion of the synthesized DNA with a restriction endonuclease, followed by electrophoretic separation and detection using methods known in the art. In another alternative, the sequence of amplified RNA may be determined by DNA synthesis using a RNA-directed DNA polymerase, the first primer, and dideoxynucleoside triphosphates (Stoflet et al., 1988). In another alternative, the sequence of the amplified third template may be determined by RNA synthesis using the DNA-directed RNA polymerase used in the amplification process, and 3'-deoxyribonucleoside triphosphates (Axelrod & Kramer, 1985). In another alternative, the amplified RNA may encode a polypeptide which could be translated, in vitro. The polypeptide product of the in vitro translation could be analyzed by using an antibody.

A sample suspected of containing or known to contain the specific nucleic acid sequence is added to the reaction mixture in the form of a template nucleic acid which is capable of homogeneous and continuous amplification and may be any intermediate in the cycle set forth in FIG. 1. In particular, the template nucleic acid may be a single-stranded RNA which contains at its 5' end a sequence which is sufficiently homologous to that which is at the 3' end of the second primer, and contains a sequence which is sufficiently complementary to the first primer. A template nucleic acid of this form would function as a first template in the amplification process. Alternatively, the template nucleic acid may be a single-stranded DNA which contains at its 3' end a sequence which is sufficiently complementary to at least the 3' end of the second primer, and contains a sequence which is sufficiently homologous to that which is at the 3' end of the first primer. A template nucleic acid of this form would function as a second template in the amplification process. Alternatively, the template nucleic acid may be a double-stranded DNA, one strand of which contains at its 5' end the entire sequence of the second primer and contains a sequence which is sufficiently complementary to the first primer. The double-stranded DNA functions as a third template in the amplification process.

Although the preparation of a template nucleic acid is not part of the amplification process, the description of possible schemes for generating template nucleic acids may be useful to the application of the amplification process. It should be understood that the schemes which may be used for obtaining the template nucleic acid are not limited to the alternatives which are described herein, and it is contemplated that other methods may be used.

In one alternative, a template nucleic acid which could function as a first template could be a naturally occurring RNA or a RNA fragment which could be generated from a larger RNA molecule by using site specific hydrolysis methods known in the art (Shibahara et al., 1987).

In another alternative, a template nucleic acid which could function as a second template could be generated from a double-stranded DNA by digestion with a restriction endonuclease which has a site immediately flanking the sequence which is sufficiently complementary to the 3' end of the second primer. The resulting double-stranded DNA fragments could then be made single-stranded by using chemical or thermal denaturation methods.

In another alternative, a template nucleic acid which could function as a second template could be generated from a single-stranded DNA or RNA to which has been hybridized an oligonucleotide which is capable of blocking DNA synthesis. This blocking oligonucleotide may contain a chemical group, which could covalently bind to the template, under the appropriate conditions. DNA synthesis from this blocked template using the first primer could result in a synthesized DNA with the same 3' end as the second template. If the original template is RNA, then the resulting DNA-RNA hybrid may be used directly as a template nucleic acid. If the original template is DNA, then the resulting copy of the second template could then be separated from the original template by using chemical or thermal denaturation methods.

In another alternative, a template nucleic acid which could function as a third template could be generated from a single-stranded DNA or RNA by DNA synthesis from the DNA or RNA template using the second primer. The resulting synthesized DNA could then be separated from the original template by using chemical or thermal denaturation methods. In addition, a RNA template could be hydrolyzed by using chemical or enzymatic methods. The resulting single-stranded DNA has the sequence of the second primer covalently attached to its 5' end and contains a sequence which is sufficiently complementary to the first primer. This single-stranded DNA could be converted to a transcriptionally functional double-stranded DNA by hybridizing the first primer to the single-stranded DNA, and by synthesizing a DNA sequence which is covalently attached to the first primer and complementary to the single-stranded DNA.

In a further alternative, a single-stranded DNA or RNA template could be obtained from a double-stranded DNA, double-stranded RNA or a DNA-RNA hybrid by using chemical, thermal, or possibly enzymatic methods. Then, by using one of the alternative schemes proposed above, the resulting single-stranded DNA or RNA could then be used to generate a template nucleic acid which could function as a first, second or third template. In addition, an alternative scheme involving the first primer and one strand of nucleic acid, and another alternative scheme involving the second primer and the other (complementary) strand of the nucleic acid may be Used concurrently to generate template nucleic acids.

MATERIALS AND METHODS

Materials

Oligonucleotides were synthesized using an Applied Biosystems 380A DNA synthesizer. Columns, phosphoramidites, and reagents used for oligonucleotide synthesis were obtained from Applied Biosystems, Inc. through Technical Marketing Associates. Oligonucleotides were purified by polyacrylamide gel electrophoresis followed by DEAE cellulose chromatography. The radioisotope [ −32p] UTP (800 Ci/mmol) was from Amersham. Enzymes for digesting and ligating DNA were purchased from New England Biolabs, and used according to the supplier's recommendations. Preparations containing the large fragment of DNA polymerase 1 (Klenow) were also purchased from New England Biolabs. RNasin and T7 RNA polymerase from Promega Biotec were purchased through Bio/Can Scientific Inc. Reverse transcriptase and RNase H were obtained from Pharmacia. The supplier for proteinase K was Boehringer Mannheim Canada. *E. coli* strain HB101 (ATCC 33694) was used for all transformations. The plasmid pUC19 (Norrander et al., 1983) was purchased from Bethesda Research Laboratories.

Isolation of DNA and sequencing

*E. coli* transformants were grown on YT medium (Miller, 1972) containing 50 ug/ml ampicillin. Plasmid DNA was purified by a rapid boiling method (Holmes and Quigley, 1981). DNA fragments and vectors used for all constructions were separated by electrophoresis on low melting point agarose, and purified from the molten agarose by phenol extraction and ethanol precipitation (Maniatis et al., 1982). Plasmid DNA was sequenced using a modification (Hattori et al., 1985) of the dideoxy method (Sanger et al., 1977). Reactions were run using the −20 universal primer (New England Biolabs).

TCA precipitation

Aliquots (5 ul) of amplification reactions were quenched in 20 ul 10 mM EDTA and placed on ice until all time point samples had been collected. The quenched samples were then applied to glass filter discs, and immediately dropped into ice-cold 5% trichloroacetic acid ("TCA") - 1% sodium pyrophosphate for 10 min with occasional mixing. Two 5 min washes with ice-cold 5% TCA were followed by two additional washes with 95% ethanol and lyophilization to dryness. Radioactivity was determined in a liquid scintillation counter.

Polyacrylamide gel electrophoresis

Samples (1 to 6 ul) were mixed with 4–5 ul formamide dye (90% deionized formamide, 10 mM TrisHCl (pH 8.0), 1 mM EDTA, xylene cyanol and bromophenol blue), and applied to a pre-run 12-cm- long 7% denaturing polyacrylamide gel. Gels were run at 350 volts until the bromophenol blue dye had reached the bottom. In some cases the gels were fixed and dried prior to autoradiography. Fixing involved a 15 min wash in 10% methanol- 7% acetic acid. The profiles of the RNA products separated by this procedure were visualized by autoradiography at room temperature.

EXAMPLE 1

Design and Synthesis of Oligonucleotides for a Gag Test System

Figure 2A:
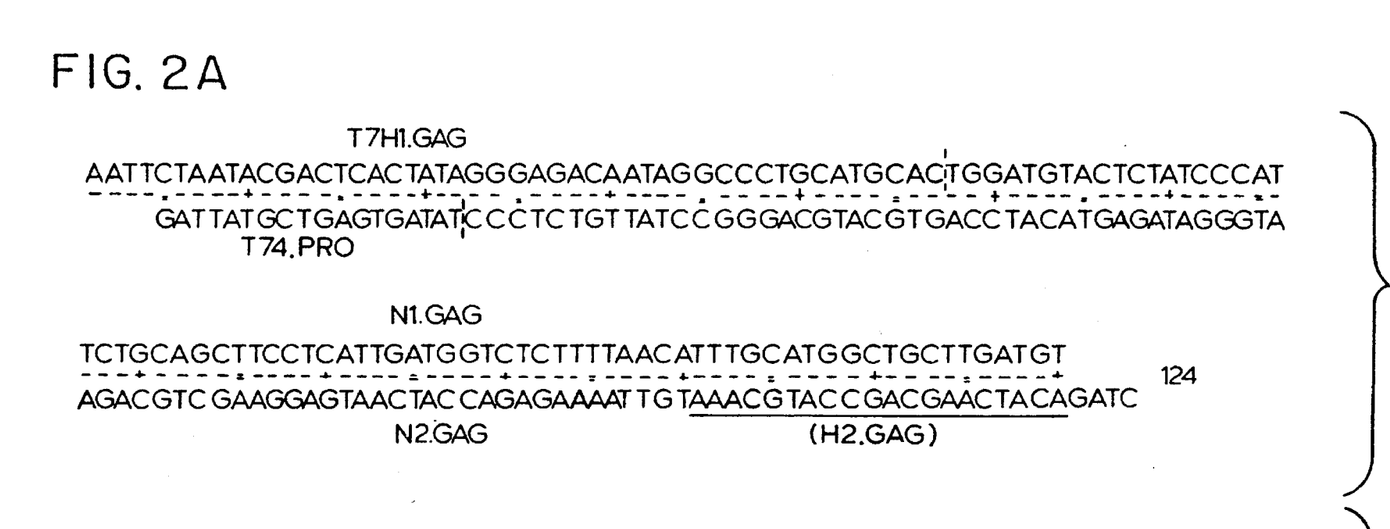
FIG. 2A, the gag test sequence.

A synthetic DNA sequence (FIG. 2A) was designed to include an EcoRI site, a T7 phage promoter, a sequence required for initiation of transcription by T7 RNA polymerase and a 19 bp hybridization region (hybridization region 1). The 47 b antisense strand oligonucleotide (T7H1.GAG) involved in the cloning of these elements also serves as the first primer. Hybridization region 2 lies 53 bp away from hybridization region 1 and is 20 bp in length. The primer made to this region (H2.GAG) is a 20 b oligonucleotide duplicate of the sense strand and is not used for cloning. The sequence spanning and including the hybridization regions is a 92 bp segment of the gag portion of the HTLV-III genome, the causative agent of AIDS. This particular gene segment was chosen because the primers were predicted to hybridize efficiently and because the distance between the two hybridization regions was relatively short. In addition, a XbaI site was placed at the end of the sequence for cloning ease. The gag test sequence test sequence also contains SphI and PstI sites which can aid in the screening of recombinants.

A total of four oligonucleotides were used in the cloning of this fragment. N1.GAG, used in the construction of both the gag test and the gag2 test sequence, completes the antisense strand and is used only in the cloning process. Similarly, T74.PRO is the sense strand component of the T7 promoter. N2.GAG however, was used in the construction of both test fragments, and has also been used as an intermediate (second template) in two steps of the amplification cycle. The entire cloned gag test fragment can also represent an intermediate of the amplification cycle (third template). Once cloned into an appropriate vector the gag test DNA could be transcribed by T7 RNA polymerase to produce a RNA fragment (first template) useful as an amplification intermediate involved in three of the steps. In addition, T7H1.GAG and H2.GAG serve as primers in the test system.

Figure 2B:
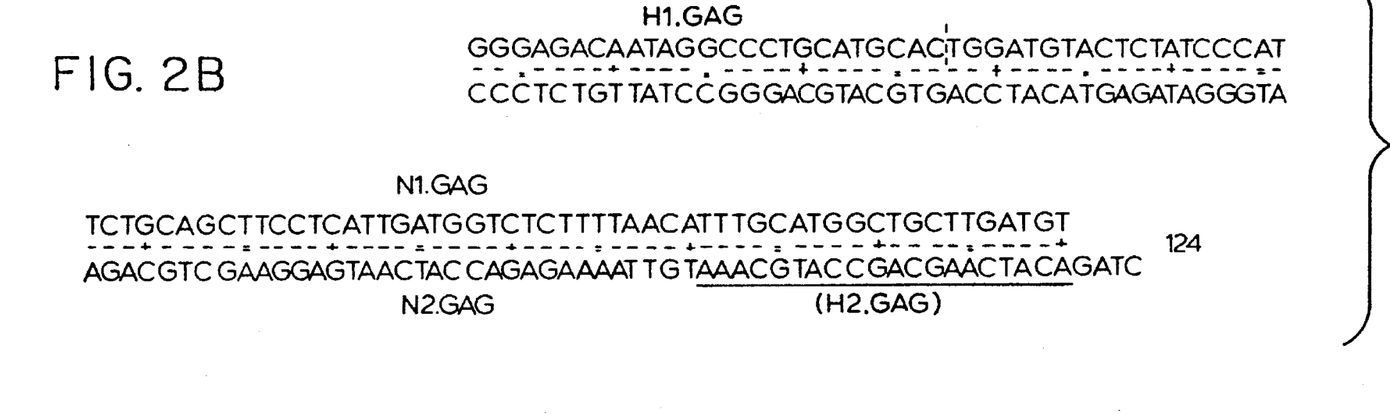
FIG. 2B, the gag2 test sequence.

The gag2 test synthetic DNA fragment (FIG. 2B) does not contain the T7 promoter, but the remainder of the sequence is identical to the gag test sequence and therefore, both N1.GAG and N2.GAG were involved in its construction. The oligonucleotide required to complete the antisense strand is called H1.GAG. Once cloned, the gag2 test fragment can be used as a template for testing amplification, using a DNA restriction fragment as template nucleic acid.

EXAMPLE 2

Construction of the Gag Test Plasmids

The oligonucleotides T74.PRO and N1.GAG (2 ug each), were phosphorylated separately in 20 ul reactions containing 70 mM TrisHCl (pH 7.6), 10 mM $MgCl_2$, 5 mM DTT, 0.5 mMATP and 5 units T4 polynucleotide kinase, at 37° C. for 30 min. Phosphorylated T74.PRO and N1.GAG (10 ul of each) were mixed with 1 ug each of unphosphorylated T7H1.GAG and N2.GAG, and 3 ul 100 mM TrisHCl (pH7.8) - 500 mM NaCl, in a final volume of 29 ul for the gag test assembly. The gag2 test mixture contained 10 ul phosphorylated N1.GAG, 1 ug each of unphosphorylated H1.GAG and N2.GAG, and 1.8 ul 100 mM TrisHCl (pH 7.8) - 500 mM NaCl, in a final volume of 18 ul. The oligonucleotide mixtures were hybridized separately by placing them at 90° C. for 10 min followed by slow cooling to room temperature for 10 to 16 h 60 ul reactions containing 50 mM TrisHCl (pH 7.8), 10 mMMgCl$_2$, 20 mM DTT, 1 mM ATP and 50 ug/ml BSA were used to ligate the hybridized oligonucleotides together. 400 units T4 DNA ligase was added to the gag test reaction and it was incubated at 15° C. for 2 h while the gag2 test reaction was incubated for 14 to 16 h with 200 units T4 DNA ligase.

The isolated and purified synthetic DNA segments were mixed with plasmid pUC19 which had been linearized by digestion at restriction enzyme sites within the polylinker region. T4 DNA ligase was used to ligate the gag test sequence into the EcoRI- XbaI fragment of pUC19, while the gag2 test sequence was ligated to the SmaI-XbaI fragment. Plasmid DNA from transformants obtained after these reactions were used to transform *E. coli* were screened by restriction analysis, and the final plasmids (pGAG.TEST and pGAG2.TEST) were determined to be correct by sequence analysis.

EXAMPLE 3

Effect of Primer Concentration on RNA Amplification

Figure 3:
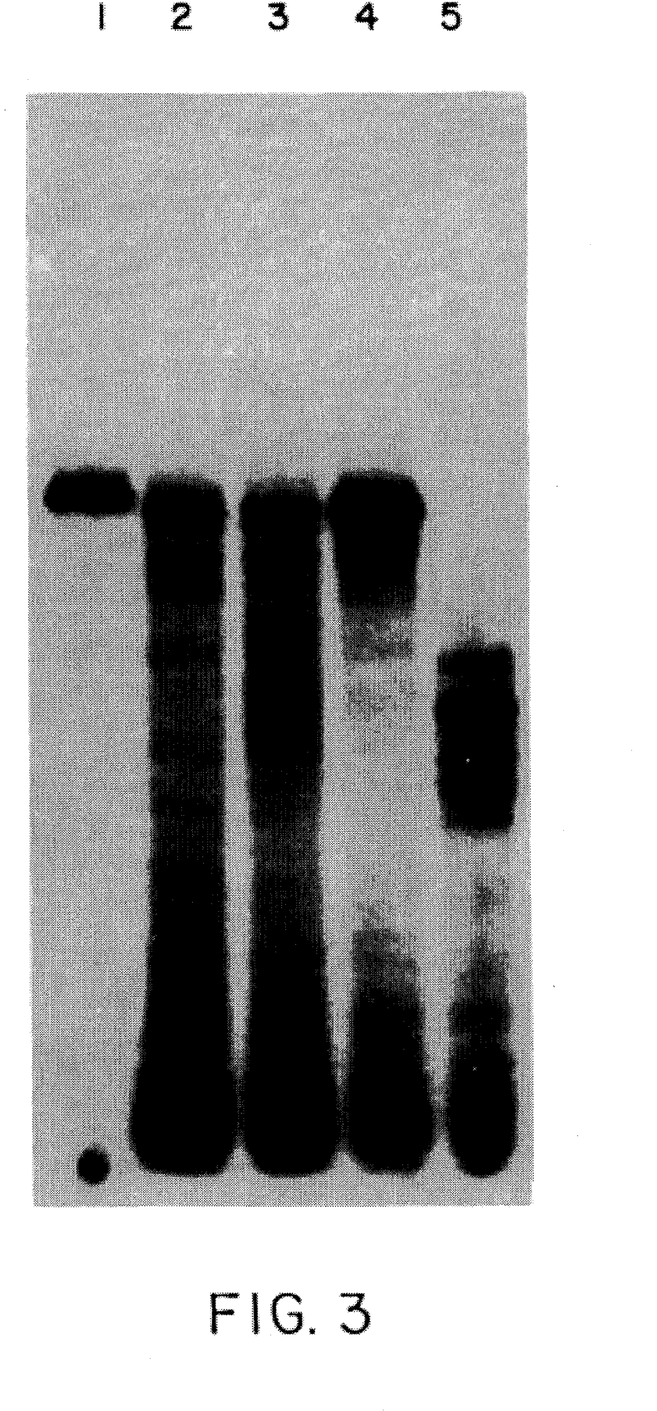
FIG. 3 is an autoradiogram of PAGE analysis of amplification reactions using different primer concentrations.

The reaction mixtures (25 ul) which were used to amplify RNA transcribed from the gag test oligonucleotides contained 50 mM TrisHCl (pH 8.45), 6 mMMgCl$_2$, 40 mM KCl, 10 mM dithiothreitol, 0.5 mM NTP (ATP, CTP, GTP, UTP), 1 mM dNTP (dATP, dCTP, dGTP dTTP), 20 units RNasin, 10 units T7 RNA polymerase, 10 units reverse transcriptase, 0.4 units RNase H, and 10 uCl [ −32p] UTP. Two of the reactions contained 0.5 ng (0.015 pmoles) N2.GAG while the other two reactions contained no template. The primers T7H1.GAG and H2.GAG were each added at final concentrations of 3.4 uM or 0.34 uM to reactions containing either N2.GAG or no template. The reactions were incubated at 42° C. for 2 h. Total synthesis of RNA was monitored by determining the incorporation of TCA insoluble cpm at 30 min. intervals. The effect of the primer concentration on template-dependent RNA synthesis is shown in Table 1. Aliquots of each reaction, containing equal amounts of synthesized RNA, were analyzed by PAGE and autoradiography (FIG. 3, lanes 1–4 numbered the same as the reactions).

TABLE 1

RNA amplification from N2.GAG after 2 h.

| Reaction | Concentration of each primer (uM) | Template (ng) | RNA Synthesized (ug) |
|---|---|---|---|
| 1 | 3.4 | 0.5 | 2.8 |
| 2 | 3.4 | — | 2.1 |
| 3 | 0.34 | 0.5 | 1.8 |
| 4 | 0.34 | — | 0.7 |

It was found that while reaction 1 resulted in the greatest incorporation of isotope, the no template control, reaction 2, was also high (73% of reaction 1) and produced a very similar electrophoretic profile. It would therefore appear that in the presence of high primer concentrations, a RNA transcript of identical size to that expected in amplification is produced in the absence of any template. Results using samples with a 10-fold decrease in primer concentration were dramatically different. The amount of RNA produced in reaction 3 was 2.6 times that of reaction 4, but while virtually all of the transcript was found in a single band of the expected size in reaction 3, no fragments greater than 60 to 70 b were found in reaction 4. Primer concentration therefore plays a significant role in the accuracy and efficiency of RNA amplification.

A control RNA transcript used to represent the size of fragment expected to be generated by the amplification system (lane 0 of FIG. 3) was prepared by transcription from the test plasmid. pGAG.TEST was linearized by digestion with XbaI, proteinase K treated (Maniatis et al., 1982), phenol extracted and ethanol precipitated. T7 RNA polymerase was then used according to the supplier's recommendations to transcribe 0.5 ug of the resulting fragment in a 25 ul reaction mixture containing 10 uCi [ −32p] UTP.

EXAMPLE 4

Effect of Template Concentration on RNA Amplification

The standard 50 ul reaction mixture used to amplify RNA transcribed from the gag test oligonucleotides contained 0.34 uM T7H1.GAG, 0.34 uM H2.GAG, 50 mM TrisHCl (pH 8.45), 6 mMMgCl$_2$, 40 mM KCl, 10 mM DTT, 0.5 mM NTP, 1 mM dNTP, 40 units RNasin, 20 units T7 RNA polymerase, 20 units reverse transcriptase, 0.8 units RNase H and 10–20 uCi [ −32p] UTP. The reactions contained amounts of template (N2.GAG) varying from 1 ng to 1 fg. One reaction contained no template. The reactions were incubated at 42° C. for 3 h, during which total synthesis of RNA was monitored by determining the incorporation of TCA insoluble cpm at 30 min intervals. As indicated in Table 2, total RNA synthesis was higher than the no template control for all template concentrations tested. Although the total synthesis of RNA generally decreased with decreasing template concentration, this decrease in synthesis was not quantitative. Thus, the degree of amplification of RNA per starting template generally increased with decreasing template concentration. Amplification of $8 \times 10^8$ fold was achieved by synthesis of 0.8 ug RNA from 1 fg of N2.GAG template. One fg of the 102-b N2.GAG oligonucleotide represents approximately $2 \times 10^4$ molecules.

TABLE 2

RNA amplification from N2.GAG after 3 h.

| Reaction | Template | RNA Synthesized (ug) | Fold amplification |
|---|---|---|---|
| 1 | 1 ng | 3.5 | $3.5 \times 10^3$ |
| 2 | 100 pg | 4.4 | $4.4 \times 10^4$ |
| 3 | 10 pg | 4.1 | $4.1 \times 10^5$ |
| 4 | 1 pg | 3.0 | $3.0 \times 10^6$ |
| 5 | 100 fg | 2.7 | $2.7 \times 10^7$ |
| 6 | 10 fg | 1.9 | $1.9 \times 10^8$ |
| 7 | 1 fg | 0.78 | $7.8 \times 10^8$ |
| 8 | — | 0.046 | — |

Figure 4:
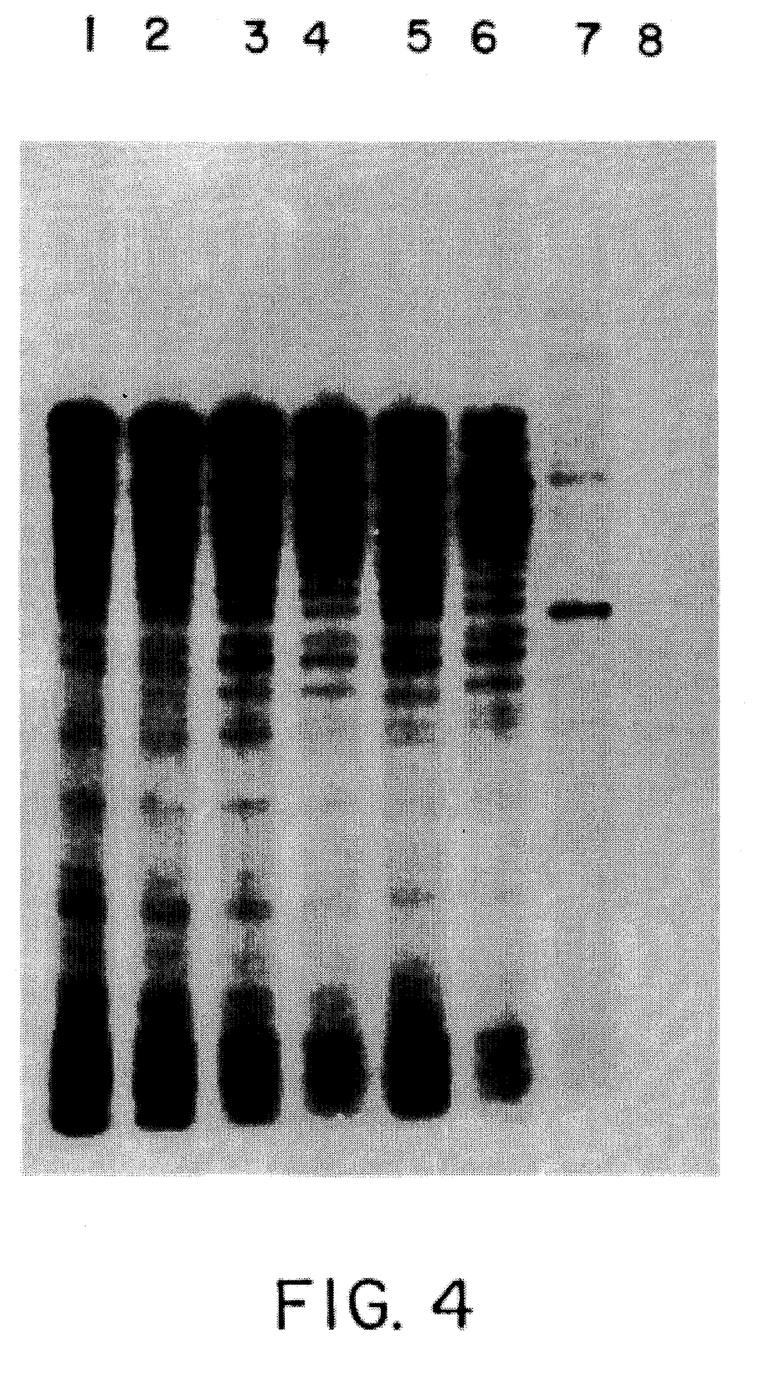
FIG. 4 is an autoradiogram of PAGE analysis of amplification reactions using different template concentrations.

The RNA which was synthesized after a reaction time of 3 h was analyzed by PAGE, for each template concentration (FIG. 4 lanes 1–8, numbered the same as the reactions). A major band representing a RNA of about 100 b was present in all reactions except the ones containing 1 fg template and no template. The reaction containing 1 fg template did not have much of this 100 b product at 3 h but the overall RNA synthesis was higher than and qualitatively different from the no template reaction.

EXAMPLE 5

Hybridization Analysis of RNA Products

Amplification reactions containing amounts of N2.GAG template varying from 1 pg to 0.1 fg were performed following the teaching of example 4, except the radiolabeled UTP was omitted. The reactions were incubated at 42° C. for 3 h. Aliquots were removed from each reaction at 30 min intervals and applied to a nylon membrane (Amersham). The nucleic acids that were contained in these reaction aliquots were fixed by exposure to ultraviolet light. The membrane was prehybridized at 50° C. for 1 h in prehybridization buffer consisting of a final concentration of 50% v/v formamide, 5 X SSC and 5 X Denhardt's solution (Maniatis et al, 1982; Southern et al, 1975) at a volume equivalent to 5 mls of solution per 100 cm$^2$ and hybridized with a radiolabeled probe with a specific activity of $10^6$ cpm/ml of hybridization solution. Hybridization was performed at 50° C. for 16 h in 50% formamide, 5 X SSC and 5 X Denhardt's solution (Maniatis et al, 1982; Southern et al, 1975). The radiolabeled probe was the synthetic oligonucleotide 5' GATCTGG-GATAGAGTACATCCA 3' which had been labeled at the 5' end using T4 polynucleotide kinase and ( −32p) ATP. After the membrane was washed at 50° C. in a series of 2, 3 min. washes consisting of 2 X SSC, 0.1% v/v SDS and 0.2 X SSC, 0.1% v/v SDS (Southern et al, 1975; Maniatis et al, 1982; Szostak et al, 1979).

Figure 5:
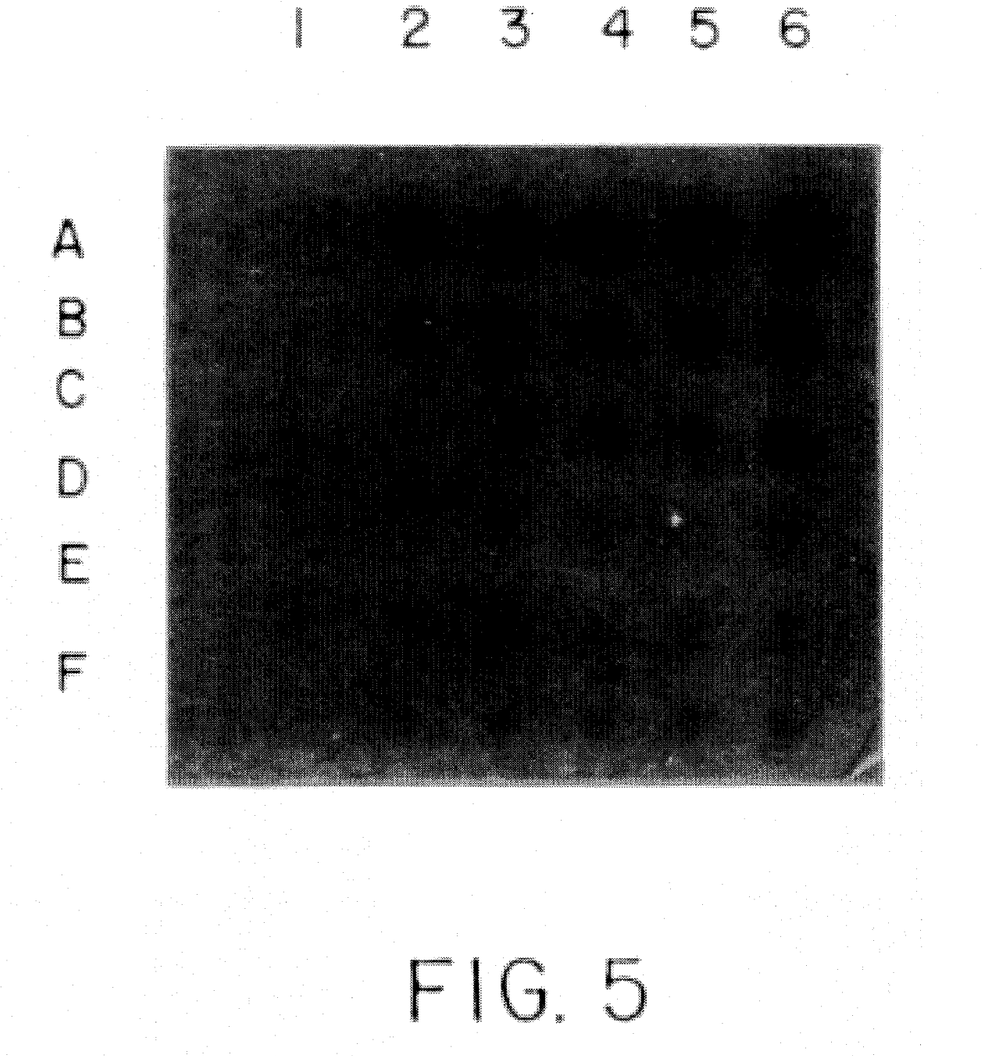
FIG. 5 is an autoradiogram of Dot-blot hybridization on amplification reactions.

FIG. 5 shows the results of the hybridization analysis performed on the amplification reactions, containing various amounts of N2.GAG template, which were sampled at different times of incubation.

Each column of FIG. 5 represents a different time point (1, 30 min; 2, 60 min; 3, 90 min; 4, 120 min; 5, 150 min; 6, 180 min) and each row represents a different amount of added N2.GAG template (1, 1 pg; 2, 100 fg; 3, 10 fg; 4, 1 fg; 5, 0.1 fg; 6, no template). Amplification of nucleic acids which hybridized to the labeled probe were observed for rows 1–3 (1 pg–10 fg), however the hybridization to specific nucleic acids in rows 4–5 (1 fg, 0.1 fg) was not higher than row 6 (no template). The apparent non-specific binding of labeled probe in row 6 seems to be related to DNA or RNA synthesis since the hybridization signal increases with increasing time.

EXAMPLE 6

Use of DNA Restriction Fragment as Template

The plasmid pGAG2.TEST was digested with MspI, treated with proteinase K, purified by phenol extraction and ethanol precipitation, and denatured by boiling for 5 min. Amplification reactions were performed and analyzed following the teaching of Example 4, except the MspI digested pGAG2.TEST was used as a template instead of the N2.GAG oligonucleotide. The amounts of plasmid added to each reaction varied from 55 ng to 5.5 pg, and no template. To simulate additional DNA which would be present in an actual sample, alternate reactions contained 1 ng of calf thymus DNA which had been similarly digested, purified and denatured. After a 3 h incubation at 42° C., the synthesis of RNA was determined by TCA precipitation and PAGE analysis. As indicated in Table 3, total RNA synthesis was higher than the no template controls for all template concentrations tested. The degree of amplification was calculated based on RNA synthesis from the actual template which was 1.8% of the total plasmid DNA.

The total RNA synthesis (degree of amplification) from a particular initial level template concentration was consistently lower for the restriction fragment (Table 3) as compared to that for the synthetic oligonucleotide template (Table 2). This could be due to competition with the complementary strand of the restriction fragment template under the conditions used.

TABLE 3

| | RNA amplification from MspI-digested pGAG2.TEST | | |
|---|---|---|---|
| Reaction | Template* | RNA Synthesized** | Fold amplification** |
| 1 | 55.0 ng [1 ng] | 3.65 | $3.7 \times 10^3$ |
| 2 | | (4.05) | $(4.1 \times 10^3)$ |
| 3 | 5.5 ng [100 pg] | 3.54 | $3.5 \times 10^4$ |
| 4 | | (3.16) | $(3.2 \times 10^4)$ |
| 5 | 550.0 pg [10 pg] | 2.29 | $2.3 \times 10^5$ |
| 6 | | (2.79) | $(2.8 \times 10^5)$ |
| 7 | 55.0 pg [1 pg] | 2.62 | $2.6 \times 10^6$ |
| 8 | | (0.67) | $(0.7 \times 10^6)$ |
| 9 | 5.5 pg [100 fg] | 1.37 | $1.4 \times 10^7$ |
| 10 | | (2.26) | $(2.3 \times 10^7)$ |
| 11 | — | 1.25 | — |
| 12 | | (0.08) | |

*Numbers in brackets indicate equivalent amounts of N2.GAG.
**Numbers in parentheses indicated RNA synthesis in presences of 1 ug MspI-digested calf thymus DNA.

Figure 6:
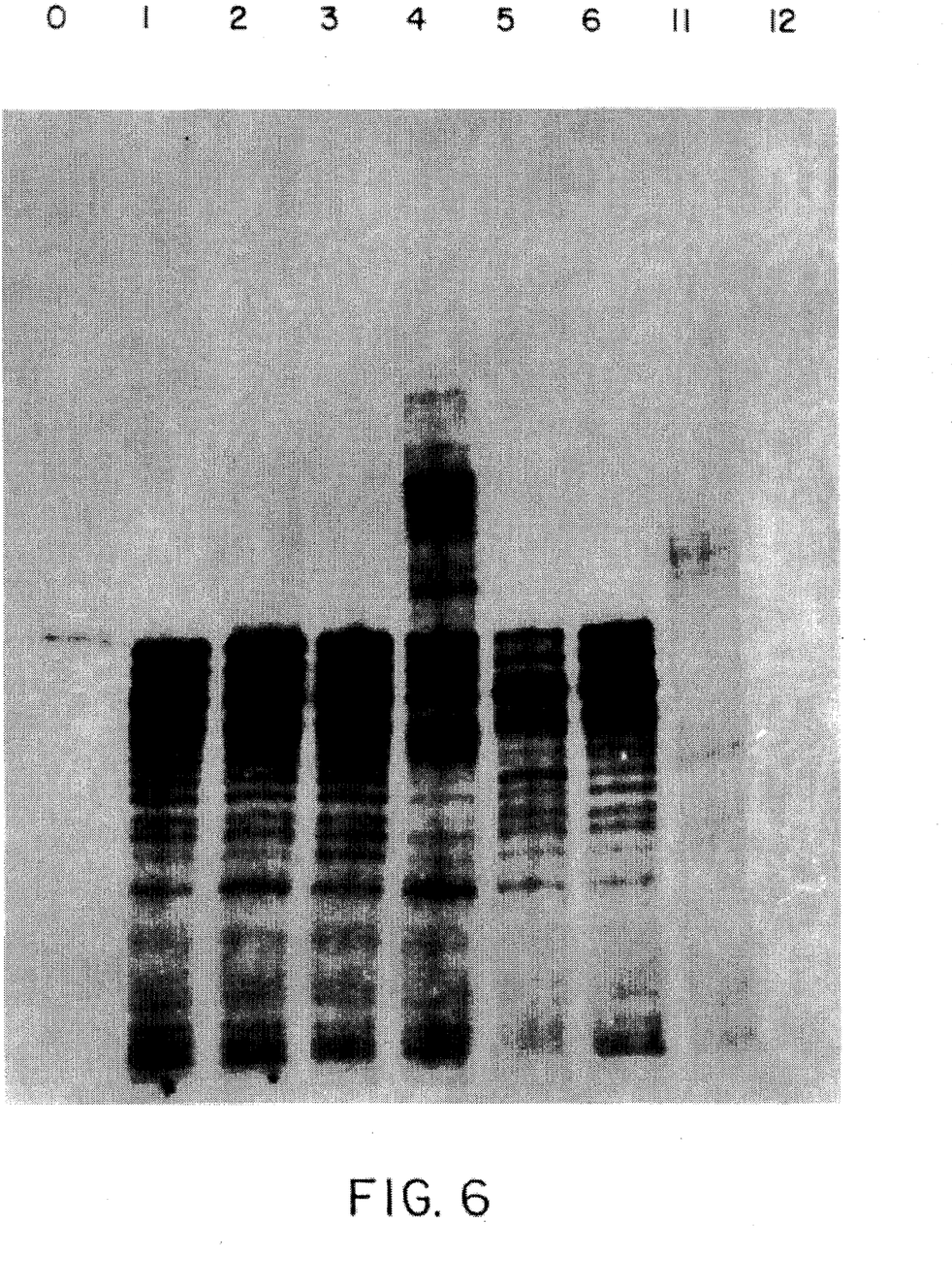
FIG. 6 is an autoradiogram of PAGE analysis of amplification reaction using restriction fragments as template.

The RNA which was synthesized after a reaction time of 3 h was analyzed by PAGE (FIG. 6, lanes 1–6, 11, and 12, numbered the same as the reactions). The major band representing a RNA of about 100 b was present in reactions (lanes) 1–6 but absent in the no template reactions (lanes 11 and 12). The RNA in lane 0 was a standard, which was prepared following the teaching of Example 3. There was no apparent qualitative difference in the synthesized RNA either with (lanes 2, 4 and 6) or without (lanes 1, 3, and 5) the additional of 1 ug of MspI-degested calf thymus DNA.

EXAMPLE 7

Use of RNA Fragment as Template

The plasmid pGAG.TEST is digested with XbaI, treated with proteinase K, and purified by phenol extraction and ethanol precipitation. RNA of a sequence complementary to N2.GAG is transcribed from the linearized pGAG.TEST plasmid using T7 RNA polymerase. The resulting RNA is purified by digestion with DNase (Pro Mega BioTec), followed by phenol extraction and ethanol precipitation. The purified RNA is used as a template for amplification reactions following the teaching of Example 5. Amounts of RNA are added to each reaction and vary from 55 ng to 5.5 pg, and no template. After a 3 h incubation at 42° C., the synthesis of specific RNA is determined by hybridization to labeled oligonucleotide probe, following the teaching of Example 5.

EXAMPLE 8

Use of Ribosomal RNA as a Template; Amplification of Internal Sequences

Two primers are used for amplifying RNA sequences which are complementary to a part of *E. coli* 16S ribosomal RNA (rRNA). One of these primers T7HIRIB3.PR2 (AATTCTAATACGACTCACTATAGGGAGTATTACCGCGGCTGCTG) contains the antisense strand of the T7 promoter and initiation site, and a sequence which is complementary to 16S rRNA. The other RIB8.PR (AATACCTTTGCTCATTGACG) is complementary to the DNA synthesized by using T7H1RIB3.PR2 as a primer and 16S rRNA as a template. A third synthetic oligonucleotide RIB5.PR (AGAAGCACCGGCTAAC) which allows detection of amplification is complementary to the RNA products of the amplification reaction, which are in turn complementary to the original rRNA template.

Reaction mixtures (25 ul) contain 50 mM TrisHCl (pH 8.45), 6 mMMgCl$_2$, 40 mM KCl, 10 mM DTT, 0.5 mM NTP, 1 mM dNTP, 20 units RNasin, 10 units T7 RNA polymerase, 10 units AMV reverse transcriptase, 0.4 units RNase H, 0.34 um T7H1RIB3.PR2, and 0.34 um RIB8.PR.

Amounts of *E. coli* rRNA varying from 50 ng to 50 fg are added to the reactions. One reaction contains no added rRNA. The reactions are incubated at 42° for 3 h, during which aliquots are removed at 30, 60, 120, and 180 minutes. The reaction aliquots are quenched, fixed to a nylon membrane, and hybridized to the $^{32}$p 5'-end labeled RIB5.PR probe, following the teaching of Example 5.

EXAMPLE 9

Use of Ribosomal RNA as a Template; Amplification of 5'-Terminal Sequences

Two primers are used for amplifying RNA sequences which are homologous to a part of *E.coli* 16S rRNA. One of these primers RIB12.PR (TTACTCACCCGTCCGCC) is complementary to 16S rRNA. The other T7H1RIB5.PR (AATTCTAATACGACTCACTATAGG-GAGAAATTGAAGAGTTTGATCAT) is complementary to the 3'end of the DNA synthesized by using RIB12.PR as a primer and 16S rRNA as a template. A third synthetic oligonucleotide RIB11.PR (GTTCGACTTGCATGTGT-TAGGCCTGCCGCCAGCGTTCAATCTGAGCC) which allows detection of amplification is complementary to both the RNA products of the amplification and the original rRNA template. The amplification reactions for rRNA and detection of the synthesized RNA are performed following the teaching of Example 8, except that T7H1RIB5.PR and RIB12.PR are used as primers (in place of T7H1RIB3.PR2 and RIB8.PR) and RIB11.PR is used as an oligonucleotide probe (in place of RIB5.PR).

Although preferred embodiments of the invention have been described in detail, it will be understood by those skilled in the art that variations may be made thereto without departing from either the spirit of the invention or the scope of the appended claims.

References

Axelrod, V. D. and Kramer, F. R. (1985) Biochemistry 24:5716–5723.

Hattori, M., Hidaka, S., and Sakaki, Y. (1985) Nucleic Acids Res. 13:7813–7827.

Holmes, D. S. and Quigley, M. (1981) Anal. Biochem. 114:193–197.

Maniatis, T., Fritsch, E. F., and Sambrook, J. (1982) Molecular Cloning. A Laboratory Manual. Cold Spring Harbor Laboratory, Cold Spring Harbor, N.Y.

Miller, J. H. (1972) Experiments in Molecular Genetics, p. 433. Cold Spring Harbor Laboratory, Cold Spring Harbor, N.Y.

Sanger, F., Nicklen, S., and Coulson, A. R. (1977) Proc. Natl. Acad. Sci. U.S.A. 74:5463–5467.

Shibahara, S., Mukai, S., Nishihara, T., Inoue, H., Ohtsuka, E., and Morisawa, H. (1987) Nucleic Acid Res. 15:4403–4415.

Southern, E. (1975) J. Mol. Biol. 98:503.

Stoflet, E. S., Koebarl, D. D., Sarkar, 6, and Sommer, 5.5. (1988) Science 239:491–494.

Szostak, J. W., Stiles, J. I., Tye, B. -K., Chiu, P., Shemran, F., and Wu, R. (1979) Methods in Enzymology 68:419.

What is claimed is:

1. A process for the amplification of an RNA first template or a DNA second template as defined herein, at a relatively constant temperature and without serial addition of reagents, comprising
   (A) providing a single reaction medium including a first primer, a second primer having an anti-sense sequence of a promoter, an RNA polymerase that recognizes said promoter, and a DNA polymerase;
   (B) providing in said single reaction medium said RNA first template, such that the following steps take place:
      (1) hybridizing said first primer to said RNA first template,
      (2) synthesizing from said DNA polymerase and said RNA first template a DNA second template by extending said first primer and thereby forming an RNA-DNA hybrid intermediate,
      (3) hydrolyzing the RNA of said RNA-DNA hybrid intermediate,
      (4) hybridizing said second primer to said DNA second templates
      (5) synthesizing from said DNA polymerase, said second primer, and said DNA second template a functional promoter recognized by an RNA polymerase,
      (6) having said RNA polymerase recognizing said functional promoter and transcribing said DNA second template, thereby providing copies of said RNA first template,
   and thereafter
   (C) maintaining said conditions for a time sufficient to achieve a desired amplification of said RNA first template or said DNA second template.

2. The process of claim 1, wherein the ribonuclease activity of the DNA polymerase hydrolyzes the RNA of an RNA-DNA hybrid without hydrolyzing single or double-stranded RNA or DNA.

3. The process of claim 2, wherein said DNA polymerase is a viral DNA polymerase.

4. The process of claim 3, wherein said viral DNA polymerase is selected from the group consisting of arian myeloblastosis virus polymerase and Maloney murine leukemia virus polymerase.

5. The process of claim 1, wherein step (A) further comprises adding to the reaction medium a ribonuclease that hydrolyzes the RNA of an RNA-DNA hybrid without hydrolyzing single- or double-stranded RNA or DNA.

6. The process of claim 5, wherein said ribonuclease is from a bacterial cell.

7. The process of claim 6, wherein said ribonuclease comprises *Escherichia coli* ribonuclease H.

8. The process of claim 2, wherein step (A) further comprises adding to the reaction medium a ribonuclease that hydrolyzes the RNA of an RNA-DNA hybrid without hydrolyzing single or double-stranded RNA or DNA.

9. The process of claim 8, wherein said ribonuclease is from a bacterial cell.

10. The process of claim 9, wherein said ribonuclease comprises *Escherichia coli* ribonuclease H.

11. In a process for the amplification of a specific nucleic acid sequence, said process involving an RNA-DNA hybrid, and single-or double-stranded RNA or DNA, the improvement which comprises using in that process a ribonuclease that hydrolyzes the RNA of an RNA-DNA hybrid without hydrolyzing single- or double-stranded RNA or DNA.

12. The process of claim 11, wherein said ribonuclease is a viral DNA polymerase.

13. The process of claim 11, wherein said ribonuclease is a bacterial or viral ribonuclease.

14. The process of claim 11, wherein said ribonuclease is selected from the group consisting of *Escherichia coli* ribonuclease H, arian myeloblastosis virus polymerase, and Maloney murine leukemia virus polymerase.

15. The process of claim 11, wherein amplification takes place at a relatively constant temperature and without serial addition of reagents.

* * * * *